United States Patent [19]

Barger et al.

[11] 4,267,834

[45] May 19, 1981

[54] SYSTEM FOR FLUSHING A MEDICAL FLUID

[75] Inventors: Larry N. Barger, Glendale; Kenneth R. McCord, Lakewood; Claude A. Vidal, Los Angeles, all of Calif.

[73] Assignee: American Hospital Supply Corporation, Evanston, Ill.

[21] Appl. No.: 32,831

[22] Filed: Apr. 24, 1979

[51] Int. Cl.³ .............................................. A61M 5/00
[52] U.S. Cl. ............................... 128/214 F; 128/274; 251/4
[58] Field of Search ............... 128/214 R, 214 F, 227, 128/274; 251/4, 117; 222/556

[56] References Cited

U.S. PATENT DOCUMENTS

| | | | |
|---|---|---|---|
| 2,706,101 | 4/1955 | Cantor | 251/4 |
| 3,316,910 | 5/1967 | Davis | 128/227 |
| 3,675,891 | 7/1972 | Reynolds et al. | 251/117 |
| 3,934,576 | 1/1976 | Danielsson | 128/214 R X |
| 4,034,754 | 7/1977 | Virag | 128/214 R |
| 4,106,675 | 8/1978 | Taylor | 128/227 X |

FOREIGN PATENT DOCUMENTS 182656 3/1922 United Kingdom ............... 251/4 X

Primary Examiner—John D. Yasko
Attorney, Agent, or Firm—Larry N. Barger

[57] ABSTRACT

A system for continuously administering parenteral liquid, such as normal saline, to a patient while blood pressure fluctuations are continuously monitored. The system includes a flushing valve with a manually squeezable and distortable elastic tube surrounding a flow restrictor. The flushing valve is connected through a flexible tube segment to a T-connector of the system to provide for convenient one hand flexible operation. The flushing valve, flexible tube segment, and T-connector are joined as a unit for assembling into the system.

16 Claims, 4 Drawing Figures

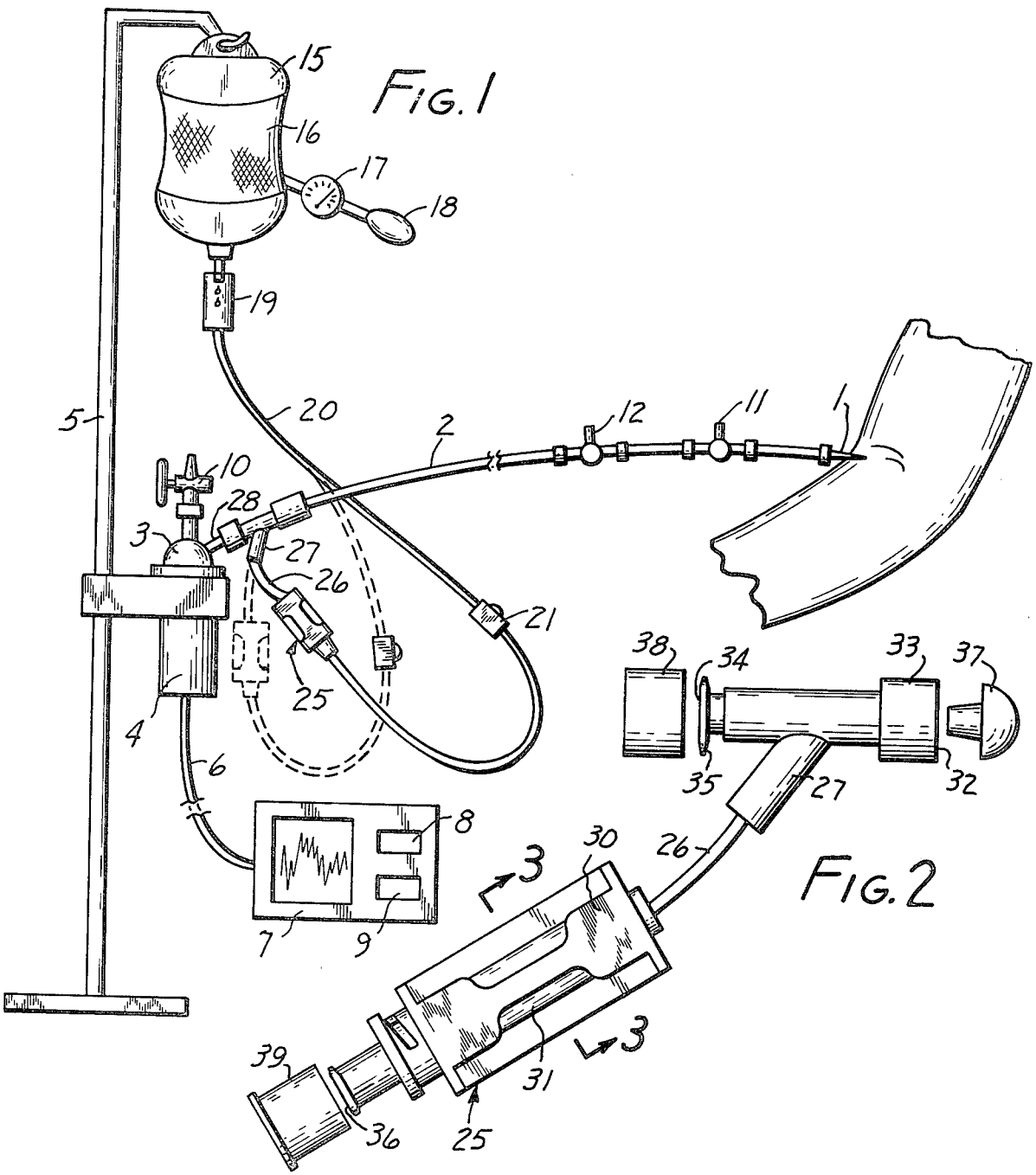
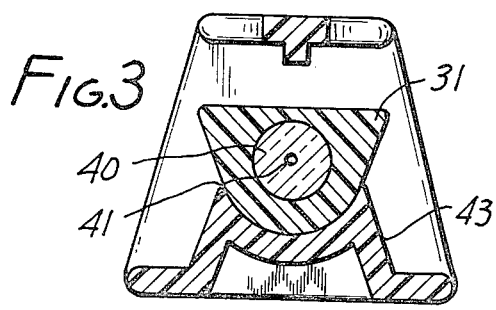
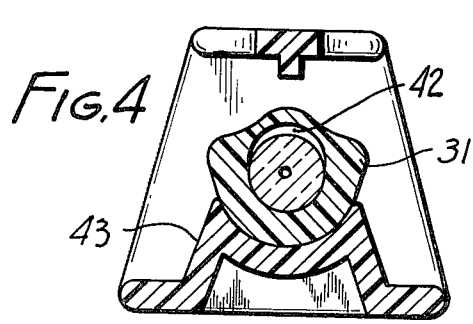

SYSTEM FOR FLUSHING A MEDICAL FLUID

BACKGROUND

U.S. Pat. No. 3,581,733 describes a system for continuously infusing a parenteral liquid, such as normal saline, into a patient at a very slow flow rate while blood pressure is continuously monitored through a pressure transducer and measuring device. This continuous infusion at a very slow flow rate is to prevent blood from entering the system and coagulating, thus interfering with a hydraulic pressure wave being sent to the pressure transducer. Periodically it is necessary to flush the system with a faster flow rate of normal saline. This is done with a stopcock 18 which transfers flow from a restricted passage 16 to a much larger passage 14, as schematically shown in the drawings of U.S. Pat. No. 3,581,733.

Another U.S. Pat. No. 3,675,891 discloses a similar system for continuously administering parenteral liquid to a patient while monitoring blood pressure fluctuations. However, this patent describes a flushing valve with an elastic pull stem. If the valve is located in a flexible line, this requires a two handed operation; i.e., one hand to hold the valve, and one to pull the stem. Enclosed is an instruction sheet for the device of U.S. Pat. No. 3,675,891 showing its use. Even if the valve is attached to a rigid pressure transducer on a supporting pole, an overly aggressive pull on the stem could upset the supporting pole, etc.

SUMMARY OF THE INVENTION

The present invention overcomes the above problems by providing a system with a flushing valve for one hand squeezing operation. This flushing valve is connected to a pressure wave transmitting tube by a short flexible tube segment and can be readily manipulated into squeezing position without disturbing the pressure wave transmission tube. The squeeze valve can be permanently connected to a T-connector and be assembled as a unit to the system. Coupling ports on the T-connector and squeeze valve of the unit are closed by protectors until assembly of the blood pressure monitoring system.

RELATED APPLICATIONS

Related co-pending co-owned applications filed on the same day as the present application are as follows:
Medical Flushing Valve and Method of Assembling Same, Filed Apr. 24, 1979, Ser. No. 032,832;
Method of Flushing A Medical Fluid, Filed Apr. 24, 1979, Ser. No. 032,830; and
Protector Housing For Squeezable Valve (Design), Filed Apr. 24, 1979, Ser. No. 032,971.

THE DRAWINGS

FIG. 1 is an elevational view of the system for continuously monitoring blood pressure with the manipulatable squeezable flushing valve;

FIG. 2 is an enlarged exploded view of a portion of the system prior to assembly showing the preconnected T-connector, squeeze valve, and removable protectors;

FIG. 3 is an enlarged sectional view taken along line 3—3 of FIG. 2 showing the valve in normal flow condition; and FIG. 4 is a view similar to FIG. 3, but showing the valve in squeezed fast flush condition.

DETAILED DESCRIPTION

In FIG. 1, a hollow patient connector 1, such as a cannula or catheter, joins to a pressure wave transmission tube 2 leading to a pressure dome 3 attached to a body 4 of a pressure transducer. This pressure transducer is rigidly supported on a pole structure 5. Within the pressure transducer is a diaphragm (not shown) against which hydraulic pressure surges from the patient's heartbeat is exerted and converted by an electrical strain member in the transducer into electrical impulses. These impulses are fed through line 6 to a monitoring instrument 7 that can include an oscilloscope, stylus and paper recorder, etc. Also if desired, instrument 7 can include other monitoring devices, such as 8 and 9, for measuring pulse rate, etc. A stopcock 10 on the transducer bleeds off air during the setup so that no air bubbles are in the system that can affect accurate pressure wave transmission.

During pressure monitoring, a liquid filled connecting tube 2 transmits heartbeat fluctuations from the patient connector 1 to the transducer. Stopcocks 11 and 12 in connecting tube 2 can be used for injecting medication into the patient or extracting a blood sample from the patient.

It is important that blood from the patient does not enter into the patient connector 1 or pressure wave transmitting tube 2 where it could coagulate and cause an erroneous pressure wave transmission. To prevent such blood coagulation, a parenteral liquid, such as normal saline, is continuously infused into the patient at a very slow flow rate. A typical flow rate might be 3 cc/hour. This parenteral liquid is infused from a fluid container 15, that is preferably of the collapsible bag type, which has a compression sleeve 16 connected to a pressure gauge 17 and a squeeze bulb 18. The parenteral liquid flows through a drip chamber 19 to a feed tube 20 that can include a conventional roller clamp 21 for opening and closing the feed tube 20. A squeezable flushing valve shown generally at 25 is permanently connected by a flexible tube segment 26 to a side port structure 27 of a rigid T-connector which is joined to a rigid adapter 28 integrally formed with the pressure dome 3. The flexible tube segment is less than 6 inches in length, so the squeeze valve is adjacent the T-connector for compact packaging of the combined valve tube segment and T-connector.

When connecting this system to a patient, and periodically throughout the continuous blood pressure monitoring procedure, it frequently becomes necessary to flush the system with the parenteral liquid at a much faster rate than the very slow flow rate being infused into the patient. When this occurs, a simple one handed squeezing action of squeeze valve 25 opens a flush passage and a surge of parenteral liquid is administered to the patient. These periodic flushings are necessary to insure that no blood is coagulating about the patient connector 1. Because of the flexible tube segment 26, the squeeze valve 25 can be manipulated into a convenient squeezing position by one hand operation. The dotted line position of the valve illustrates how it can be moved without substantially disturbing any of the remaining portions of the system. Flexible tube segment 26 also permits a certain degree of twisting of the squeeze valve for comfortable one hand squeezing action when the nurse or physician is standing at various locations about the system shown in FIG. 1.

FIG. 2 shows a portion of the system immediately prior to assembly of the system. Here a squeezable flushing valve is shown that has a protector housing 30 protecting a squeezable elastic tube 31 from inadvertent squeezing. Protector housing 30 has side openings for insertion of thumb and forefinger for intentional squeezing to flush the valve. The flushing valve is permanently connected to the flexible tube segment 26 which is in turn connected to the rigid side port 27 of a rigid thermoplastic T-connector. The T-connector has a first coupling port 32 with an internally threaded retention collar 33. Coupling port 32 is adapted to join with a mating coupler on pressure wave transmission tube 2. A second coupling port 34 on the T-connector has retaining ears 35 for coupling with the pressure transducer dome. A coupling port 36 on the flushing valve is adapted to connect with a mating coupler of feed tube 20. All three of the coupling ports in FIG. 2 are preferably closed by removable protectors 37, 38, and 39 until immediately prior to assembling the system. The portion of the system shown in FIG. 2 is conveniently sold as a separate product to be coupled with pressure transmitting tube 2, also sold as a separate product. Thus, the portion of the system shown in FIG. 2 can be coupled with pressure wave transmission tube 2 of different lengths.

In FIG. 3, the protector housing surrounds the elastic tube 31 that is generally triangular shaped. The elastic tube 31 is firmly sealed against a flow restrictor 40, which is a glass tube having a restricted bore 41, of a diameter of 0.001 to 0.004 inch. The diameter of bore 41 of 0.002 inch works very well. In FIG. 3, all parenteral liquid is forced through restricting bore 41 in glass tube restrictor 40.

When it is desired to temporarily flush the unit, the elastic tube 31 is laterally squeezed to open a flush passage 42 having a much faster flow rate than bore 41. A limit lug 43 in the form of a cradle having a concave surface protects against substantial movement of the squeeze tube 31 and thus prevents any dislodgment of flow restrictor 40 which could create air bubble pockets in the valve.

In the foregoing description, specific examples have been used to illustrate the invention. However, it is understood by those skilled in the art that certain modifications can be made to these examples without departing from the spirit and scope of the invention.

We claim:

1. A system for flushing a medical fluid that includes a pressure wave tube for coupling a patient connector with a pressure transducer, and which includes a feed tube to continuously infuse fluid to a patient through a side port of the system, wherein the improvement comprises: a flushing valve connected to the feed tube and spaced from the side port by a flexible tube segment; and the flushing valve includes an elastically distortable tube having a noncircular outer surface, and a restriction in the tube which combines with the tube to form a restricted passage means having a predetermined flow rate therethrough, said tube being distortable to temporarily form a flush passage in the valve having a substantially faster flow rate.

2. A system as set forth in claim 1, wherein the flexible tube segment is less than 6 inches in length.

3. A system as set forth in claim 1, wherein the system has a T-connector that includes a side port and the flexible tube segment is secured to the side port of this T-connector.

4. A system as set forth in claim 3, wherein the T-connector is permanently connected to the flexible tube segment, and the flexible tube segment is in turn permanently connected to one end of the flushing valve.

5. A system as set forth in claim 4, wherein the flushing valve has a coupler at its opposite end to removably connect with the mating coupler on the feed tube.

6. A system as set forth in claim 3, wherein the T-connector is rigid.

7. A system as set forth in claim 3, wherein the T-connector has two ports in addition to its side port, and these two ports each have coupling means for joining the T-connector to the system.

8. A system as set forth in claim 7, wherein the two coupling ports are closed by removable protectors prior to assembling the system.

9. A system as set forth in claim 1, wherein the pressure wave tube has means other than the side port for injecting or extracting fluid from the system.

10. A system as set forth in claim 9, wherein the pressure wave tube includes a plurality of stopcocks.

11. A system for flushing a medical fluid comprising: a T-connector having a pair of coupling ports for joining with a pressure wave conduit means, and also having a side port; a flexible tube segment joined to the T-connector's side port; and a flushing valve joined to the flexible tube segment and having a manually distortable elastic member with a noncircular outer surface, said elastic member sealingly engaging a flow restrictor and adapted to be distorted to form a flush passage.

12. A system as set forth in claim 11, wherein one coupling port includes a threaded retention collar.

13. A system as set forth in claim 11, wherein both coupling ports of the T-connector are closed by a removable protector.

14. A system as set forth in claim 11, wherein the flushing valve has a coupler at a location spaced from the valve's attachment to the flexible tube segment and the valve's coupler is closed by a removable protector.

15. A system as set forth in claim 11, wherein the flushing valve includes a restrictor with a continuously open bore therethrough.

16. A system for flushing a medical fluid which comprises: a pressure wave tube; a patient connector joined to one end of the pressure wave tube; a pressure transducer joined to an opposite end of the pressure wave tube; a side port into the pressure wave tube; a fluid pressure source; a feed tube leading from the fluid pressure source to the side port; and a flushing valve between the fluid source and the side port to control fluid flow rate through the side port; and said flushing valve includes a flow restrictor having a slow flow bore therethrough, an elastic squeezable tube with a noncircular outer surface, said tube encasing the flow restrictor and which is distortable to temporarily form a flush passage for substantially faster flow, and a protector housing on the valve with side openings providing squeezable access to the elastic tube.

* * * * *